US012243232B1

(12) United States Patent
Cogan et al.

(10) Patent No.: US 12,243,232 B1
(45) Date of Patent: *Mar. 4, 2025

(54) RACIALLY UNBIASED DEEP LEARNING-BASED MAMMOGRAM ANALYZER

(71) Applicant: MedCognetics, Inc., Dallas, TX (US)

(72) Inventors: Timothy Cogan, McKinney, TX (US); Richard Stubblefield, Diablo, CA (US); Lakshman Tamil, Plano, TX (US)

(73) Assignee: MedCognetics, Inc, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/625,028

(22) Filed: Apr. 2, 2024

Related U.S. Application Data

(63) Continuation of application No. 17/305,864, filed on Jul. 15, 2021, now Pat. No. 11,948,297.

(60) Provisional application No. 63/052,411, filed on Jul. 15, 2020.

(51) Int. Cl.
| | |
|---|---|
| *G06T 7/00* | (2017.01) |
| *A61B 6/50* | (2024.01) |
| *G06N 3/04* | (2023.01) |
| *G06N 3/08* | (2023.01) |
| *G16H 30/20* | (2018.01) |

(52) U.S. Cl.
CPC ............ *G06T 7/0012* (2013.01); *A61B 6/502* (2013.01); *G06N 3/04* (2013.01); *G06N 3/08* (2013.01); *G16H 30/20* (2018.01); *G06T 2207/20081* (2013.01); *G06T 2207/20084* (2013.01); *G06T 2207/30068* (2013.01)

(58) Field of Classification Search
CPC ......... G06T 7/0012; G06T 2207/20081; G06T 2207/20084; G06T 2207/30068; A61B 6/502; G06N 3/04; G06N 3/08; G16H 30/20
See application file for complete search history.

(56) References Cited

U.S. PATENT DOCUMENTS

| | | | | |
|---|---|---|---|---|
| 2010/0255470 A1* | 10/2010 | Bankaitis-Davis | .. | C12Q 1/6886 435/6.14 |
| 2011/0093295 A1* | 4/2011 | Mankad | ................. | G16H 10/60 705/500 |
| 2016/0246947 A1* | 8/2016 | Yao | ........................ | G16H 10/20 |

(Continued)

*Primary Examiner* — Santiago Garcia
(74) *Attorney, Agent, or Firm* — Aka Chan LLP

(57) ABSTRACT

A racially unbiased mammogram analyzer includes an interface for receiving mammograms; a processor for extracting features of mammograms of general population; a processor for extracting features of mammograms of a specific race. In one embodiment, the general population mammogram features are represented by middle layers of a CNN and the race specific features are represented by the end layer of the CNN network. In one embodiment, the race specific layers of CNN change dynamically according to the race indication done explicitly. In one embodiment the race specific layers of CNN change dynamically according to the race indication given by race indication processor. In one embodiment, the race indications are computed by a network of parallel variational autoencoder networks. In one embodiment, the race indicator computes race specific information to the CNN and are provided by variational autoencoders.

20 Claims, 7 Drawing Sheets

(56) References Cited

U.S. PATENT DOCUMENTS

| | | | | |
|---|---|---|---|---|
| 2018/0342323 A1* | 11/2018 | Shankar | ................. | G16H 10/60 |
| 2019/0138693 A1 | 5/2019 | Muller | | |
| 2019/0147592 A1* | 5/2019 | Yu | ........................ | G06V 20/695 |
| | | | | 382/128 |
| 2019/0236782 A1* | 8/2019 | Amit | ..................... | G06T 7/0016 |
| 2020/0160510 A1* | 5/2020 | Lindemer | ............. | G06F 40/216 |
| 2020/0360312 A1* | 11/2020 | Hall | ......................... | G06T 7/33 |
| 2020/0381121 A1* | 12/2020 | Wang | ................... | G06V 20/698 |
| 2021/0093249 A1* | 4/2021 | Anand | ................... | G16H 50/20 |
| 2021/0125074 A1* | 4/2021 | Lee | ....................... | G06V 20/647 |
| 2022/0084660 A1* | 3/2022 | Georgescu | .............. | G06N 3/08 |
| 2022/0117509 A1* | 4/2022 | Garff | ...................... | G16H 50/30 |
| 2022/0138949 A1 | 5/2022 | Enzmann | | |
| 2022/0292674 A1* | 9/2022 | Braman | ................ | G06T 7/0012 |
| 2022/0398724 A1* | 12/2022 | Anand | ................ | G06N 3/0464 |
| 2023/0030506 A1* | 2/2023 | Jaber | ................... | G06F 18/2413 |
| 2023/0112591 A1* | 4/2023 | Torben-Nielsen | ..... | G16H 50/20 |
| | | | | 705/3 |
| 2024/0127437 A1* | 4/2024 | Anand | ................... | G06V 10/25 |

\* cited by examiner

RACIALLY UNBIASED DEEP LEARNING-BASED MAMMOGRAM ANALYZER

CROSS-REFERENCE TO RELATED APPLICATIONS

This application is a continuation of U.S. patent application Ser. No. 17/305,864, filed Jul. 15, 2021, issued as U.S. Pat. No. 11,948,297 on Apr. 2, 2024, which claims the benefit of U.S. patent application 63/052,411, filed Jul. 15, 2020. These applications are incorporated by reference along with all other references cited in this application.

BACKGROUND OF THE INVENTION

This invention relates to automated mammogram classification and more particularly, to systems and methods for deep learning-based mammogram classification that are racially unbiased.

Worldwide, breast cancer is the most common cancer for women and the second most common cancer when considering both men and women. In addition, breast cancer is the leading cause of cancer death in women across the globe. For women as young as 40, mammograms, X-ray images of breast tissue, can provide a cost-effective means for breast cancer screening. Typically, mammograms are screened by radiologists who determine whether or not a biopsy is needed to classify a tissue abnormality as malignant or benign. Machine learning algorithms capable of performing at or above the level of a radiologist could potentially replace or assist radiologists and thereby reduce the cost of mammograms as well as lead to earlier and more reliable detection of breast cancer. For the past decade, many different machine learning algorithms have been proposed using state-of-the-art techniques to aid in the detection and classification of malignant abnormalities. In mammogram analysis as in other areas of research, deep learning has been emerging as a dominant machine learning technique because it helps deal with the challenge of feature extraction. Machine learning techniques such as support vector machines (SVMs) are effective when there is a strong feature set, but in problems such as malignancy identification there is a fundamental challenge in determining the relevant features of an abnormality. Convolutional neural networks (CNNs) are particularly effective in extracting features from images and are being leveraged in a majority of deep learning solutions in mammogram research. A few studies also leveraged Region Proposal CNN (R-CNN) method and variations of the method called Fast-CNN and Faster-CNN. These variations of R-CNN provide increasingly faster object detection than R-CNN. The performance of faster regional convolutional neural network (Faster-RCNN) architecture on the INBREAST dataset has been demonstrated by use of a VGG16 based Faster-RCNN.

All the deep learning networks developed so far have racial biases whereby performance on races not trained on is poor, for example, the false positives and false negatives are high. The machine learning algorithm that we are building here will alleviate the bias issue and the performance of our algorithm is nearly the same for all the races.

Therefore, there is a need for an improved a racially unbiased deep learning-based mammogram analyzer.

BRIEF SUMMARY OF THE INVENTION

A racially unbiased mammogram analyzer includes an interface for receiving mammograms; a processor for extracting features of mammograms of general population; a processor for extracting features of mammograms of a specific race. In one embodiment, the general population mammogram features are represented by middle layers of a CNN and the race specific features are represented by the end layer of the CNN network. In one embodiment, the race specific layers of CNN change dynamically according to the race indication done explicitly. In one embodiment the race specific layers of CNN change dynamically according to the race indication given by race indication processor. In one embodiment, the race indications are computed by a network of parallel variational autoencoder networks. In one embodiment, the race indicator computes race specific information to the CNN and are provided by variational autoencoders.

In an implementation, a system for analyzing mammograms includes a convolutional neural network (CNN) with multiple convolutional layers representing features of mammograms of general population; and a final layer of the CNN representing the features of a specific race. The multiple final layers of CNN can represent the mammogram features of a specific race. The final layers of CNN containing the features of race specific mammogram information can dynamically change according to the race information provided explicitly. The final layers of CNN containing the features of race specific mammogram information can dynamically change according to the race information provided implicitly via a race indicator. The layers of CNN containing the features of race specific mammogram information can be provided by the hidden layer of a variational auto encoder.

In an implementation, a system for predicting breast density includes a convolutional neural network (CNN) with multiple convolutional layers representing features of mammograms of general population; and a final layer of the CNN representing the features of a specific race given by a DualViewNet. Multiple final layers of CNN can represent the mammogram features of a specific race given by a variational auto encoder. The final layers of CNN containing the features of race specific mammogram information can dynamically change according to the race information provided explicitly. The final layers of CNN containing the features of race specific mammogram information can dynamically change according to the race information provided implicitly via a race indicator. The layers of CNN containing the features of race specific mammogram information can be provided by the hidden layer of a variational auto encoder.

In a implementation, a system includes a deep neural network (e.g., convolutional neural network) including a number of layers arranged in a hierarchy. An input of the convolutional neural network is at a bottom of the hierarchy of layers. An output is at a top of the hierarchy of layers. A first number or set of layers of the convolutional neural network is trained by federated learning (or other machine learning, but not active learning) using a first set of training data including first breast images including multiple ethnicities (e.g., representative of a general population of a place such as the United States).

A second layer of the convolutional neural network is trained by active learning (e.g., trained differently from that used for the first layers) using a second set of training data including second breast images from only a single ethnicity, a first ethnicity. A third layer is trained by active learning using a third set of training data including third images from only a single ethnicity, a second ethnicity that is different from the first ethnicity. The second and third layers are at the same level in the hierarchy of the convolutional neural network. The second and third layers are above the first layers of the convolutional neural network.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
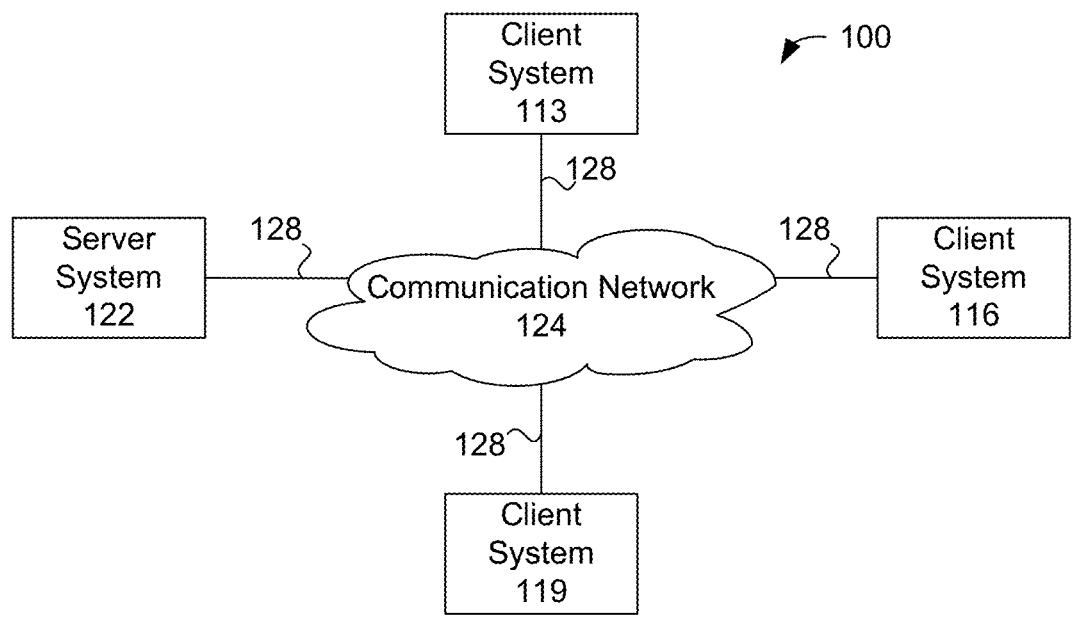
FIG. 1 shows a simplified block diagram of a client-server system implemented in a distributed computing network connecting a server and clients.

FIG. 1 is a simplified block diagram of a distributed computer network 100 incorporating an embodiment of the present invention. Computer network 100 includes a number of client systems 113, 116, and 119, and a server system 122 coupled to a communication network 124 via a plurality of communication links 128. Communication network 124 provides a mechanism for allowing the various components of distributed network 100 to communicate and exchange information with each other.

Communication network 124 may itself be comprised of many interconnected computer systems and communication links. Communication links 128 may be hardwire links, optical links, satellite or other wireless communications links, wave propagation links, or any other mechanisms for communication of information. Communication links 128 may be DSL, Cable, Ethernet or other hardwire links, passive or active optical links, 3G, 3.5G, 4G and other mobility, satellite or other wireless communications links, wave propagation links, or any other mechanisms for communication of information.

Various communication protocols may be used to facilitate communication between the various systems shown in FIG. 1. These communication protocols may include VLAN, MPLS, TCP/IP, Tunneling, HTTP protocols, wireless application protocol (WAP), vendor-specific protocols, customized protocols, and others. While in one embodiment, communication network 124 is the Internet, in other embodiments, communication network 124 may be any suitable communication network including a local area network (LAN), a wide area network (WAN), a wireless network, an intranet, a private network, a public network, a switched network, and combinations of these, and the like.

Distributed computer network 100 in FIG. 1 is merely illustrative of an embodiment incorporating the present invention and does not limit the scope of the invention as recited in the claims. One of ordinary skill in the art would recognize other variations, modifications, and alternatives. For example, more than one server system 122 may be connected to communication network 124. As another example, a number of client systems 113, 116, and 119 may be coupled to communication network 124 via an access provider (not shown) or via some other server system.

Client systems 113, 116, and 119 typically request information from a server system which provides the information. For this reason, server systems typically have more computing and storage capacity than client systems. However, a particular computer system may act as both as a client or a server depending on whether the computer system is requesting or providing information. Additionally, although aspects of the invention have been described using a client-server environment, it should be apparent that the invention may also be embodied in a stand-alone computer system.

Server 122 is responsible for receiving information requests from client systems 113, 116, and 119, performing processing required to satisfy the requests, and for forwarding the results corresponding to the requests back to the requesting client system. The processing required to satisfy the request may be performed by server system 122 or may alternatively be delegated to other servers connected to communication network 124.

Client systems 113, 116, and 119 enable users to access and query information stored by server system 122. In a specific embodiment, the client systems can run as a stand-alone application such as a desktop application or mobile smartphone or tablet application. In another embodiment, a "web browser" application executing on a client system enables users to select, access, retrieve, or query information stored by server system 122. Examples of web browsers include the Internet Explorer browser program provided by Microsoft Corporation, Firefox browser provided by Mozilla, Chrome browser provided by Google, Safari browser provided by Apple, and others.

In a client-server environment, some resources (e.g., files, music, video, or data) are stored at the client while others are stored or delivered from elsewhere in the network, such as a server, and accessible via the network (e.g., the Internet). Therefore, the user's data can be stored in the network or "cloud." For example, the user can work on documents on a client device that are stored remotely on the cloud (e.g., server). Data on the client device can be synchronized with the cloud.

Figure 2:
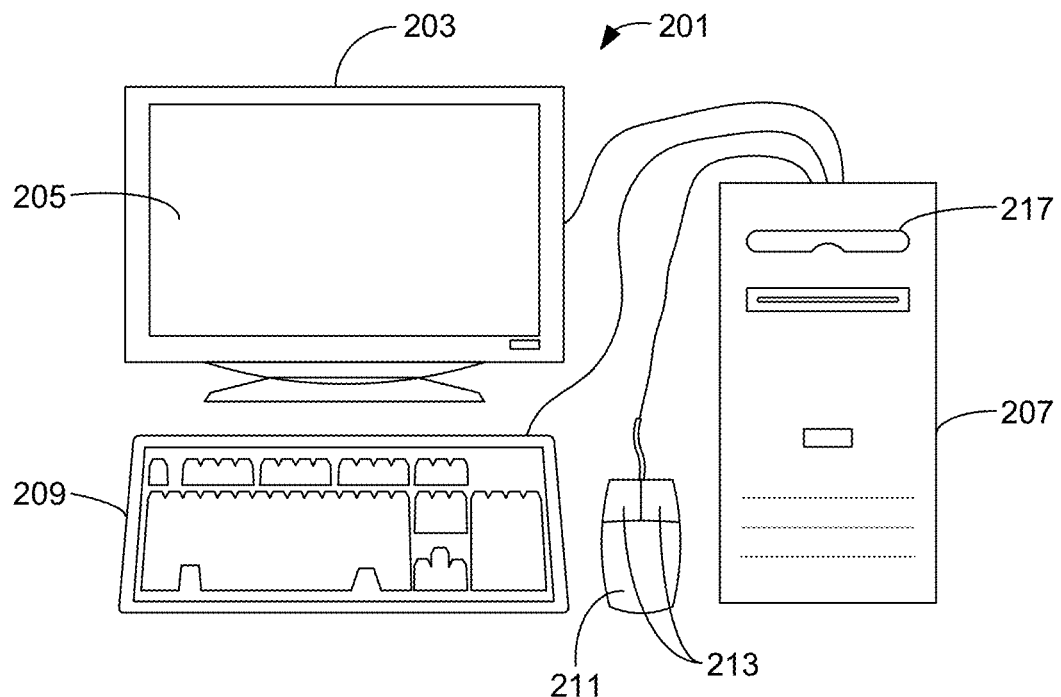
FIG. 2 shows a more detailed diagram of an exemplary client or computer which may be used in an implementation of the invention.

FIG. 2 shows an exemplary client or server system of the present invention. In an embodiment, a user interfaces with the system through a computer workstation system, such as shown in FIG. 2. FIG. 2 shows a computer system 201 that includes a monitor 203, screen 205, enclosure 207 (may also be referred to as a system unit, cabinet, or case), keyboard or other human input device 209, and mouse or other pointing device 211. Mouse 211 may have one or more buttons such as mouse buttons 213.

It should be understood that the present invention is not limited any computing device in a specific form factor (e.g., desktop computer form factor), but can include all types of computing devices in various form factors. A user can interface with any computing device, including smartphones, personal computers, laptops, electronic tablet devices, global positioning system (GPS) receivers, portable media players, personal digital assistants (PDAs), other network access devices, and other processing devices capable of receiving or transmitting data.

For example, in a specific implementation, the client device can be a smartphone or tablet device, such as the Apple iphone, Apple iPad, Apple iPod, Samsung Galaxy product (e.g., Galaxy S series product or Galaxy Note series product), Google Nexus devices, and Microsoft devices (e.g., Microsoft Surface tablet). Typically, a smartphone includes a telephony portion (and associated radios) and a computer portion, which are accessible via a touch screen display.

There is nonvolatile memory to store data of the telephone portion (e.g., contacts and phone numbers) and the computer portion (e.g., application programs including a browser, pictures, games, videos, and music). The smartphone typically includes a camera (e.g., front facing camera or rear camera, or both) for taking pictures and video. For example, a smartphone or tablet can be used to take live video that can be streamed to one or more other devices.

Enclosure 207 houses familiar computer components, some of which are not shown, such as a processor, memory, mass storage devices 217, and the like. Mass storage devices 217 may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive or solid state drive (SSD)), battery-backed-up volatile memory, tape storage, reader, and other similar media, and combinations of these.

A computer-implemented or computer-executable version or computer program product of the invention may be embodied using, stored on, or associated with computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on mass storage device 217. The source code of the software of the present invention may also be stored or reside on mass storage device 217 (e.g., hard disk, magnetic disk, tape, or CD-ROM). As a further example, code of the invention may be transmitted via wires, radio waves, or through a network such as the Internet.

Figure 3:
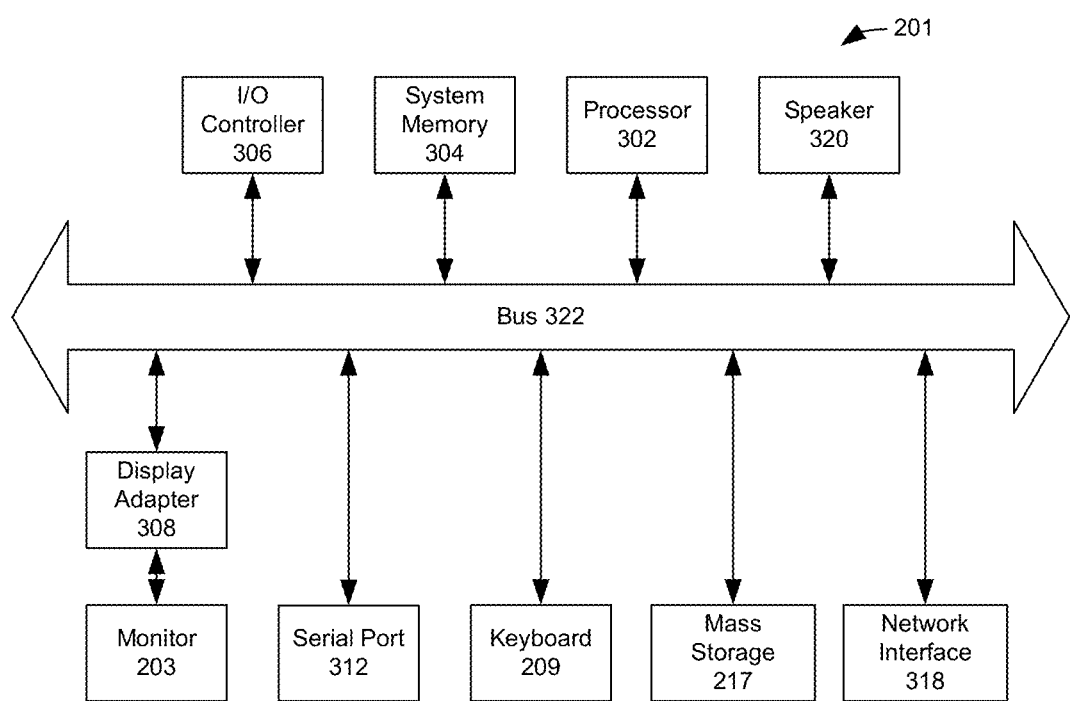
FIG. 3 shows a system block diagram of a client computer system used to execute application programs such as a web browser or tools.

FIG. 3 shows a system block diagram of computer system 201 used to execute the software of the present invention. As in FIG. 2, computer system 201 includes monitor 203, keyboard 209, and mass storage devices 217. Computer system 501 further includes subsystems such as central processor 302, system memory 304, input/output (I/O) controller 306, display adapter 308, serial or universal serial bus (USB) port 312, network interface 318, and speaker 320. The invention may also be used with computer systems with additional or fewer subsystems. For example, a computer system could include more than one processor 302 (i.e., a multiprocessor system) or a system may include a cache memory.

Arrows such as 322 represent the system bus architecture of computer system 201. However, these arrows are illustrative of any interconnection scheme serving to link the subsystems. For example, speaker 320 could be connected to the other subsystems through a port or have an internal direct connection to central processor 302. The processor may include multiple processors or a multicore processor, which may permit parallel processing of information. Computer system 201 shown in FIG. 2 is but an example of a computer system suitable for use with the present invention. Other configurations of subsystems suitable for use with the present invention will be readily apparent to one of ordinary skill in the art.

Computer software products may be written in any of various suitable programming languages, such as C, C++, C#, Pascal, Fortran, Perl, Matlab (from MathWorks, www.mathworks.com), SAS, SPSS, JavaScript, AJAX, Java, Python, Erlang, and Ruby on Rails. The computer software product may be an independent application with data input and data display modules. Alternatively, the computer software products may be classes that may be instantiated as distributed objects. The computer software products may also be component software such as Java Beans (from Oracle Corporation) or Enterprise Java Beans (EJB from Oracle Corporation).

An operating system for the system may be one of the Microsoft Windows® family of systems (e.g., Windows 95, 98, Me, Windows NT, Windows 2000, Windows XP, Windows XP ×64 Edition, Windows Vista, Windows 7, Windows 8, Windows 10, Windows 11, Windows CE, Windows Mobile, Windows RT), Symbian OS, Tizen, Linux, HP-UX, UNIX, Sun OS, Solaris, Mac OS X, Apple IOS, Android, Alpha OS, AIX, IRIX32, or IRIX64. Other operating systems may be used. Microsoft Windows is a trademark of Microsoft Corporation.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, 802.11n, 802.11ac (e.g., Wi-Fi 5), 802.11ad, 802.11ax (e.g., Wi-Fi 6), and 802.11af, just to name a few examples), near field communication (NFC), radio-frequency identification (RFID), mobile or cellular wireless (e.g., 2G, 3G, 4G, 5G, 3GPP LTE, WiMAX, LTE, LTE Advanced, Flash-OFDM, HIPERMAN, iBurst, EDGE Evolution, UMTS, UMTS-TDD, 1×RDD, and EV-DO). For example, signals from a computer may be transferred, at least in part, wirelessly to components or other computers.

In an embodiment, with a web browser executing on a computer workstation system, a user accesses a system on the World Wide Web (WWW) through a network such as the Internet. The web browser is used to download web pages or other content in various formats including HTML, XML, text, PDF, and postscript, and may be used to upload information to other parts of the system. The web browser may use uniform resource identifiers (URLs) to identify resources on the web and hypertext transfer protocol (HTTP) in transferring files on the web.

In other implementations, the user accesses the system through either or both of native and nonnative applications. Native applications are locally installed on the particular computing system and are specific to the operating system or one or more hardware devices of that computing system, or a combination of these. These applications (which are sometimes also referred to as "apps") can be updated (e.g., periodically) via a direct internet upgrade patching mechanism or through an applications store (e.g., Apple iTunes and App store, Google Play store, Windows Phone store, and Blackberry App World store).

The system can run in platform-independent, nonnative applications. For example, client can access the system through a web application from one or more servers using a network connection with the server or servers and load the web application in a web browser. For example, a web application can be downloaded from an application server over the Internet by a web browser. Nonnative applications can also be obtained from other sources, such as a disk.

Racially Unbiased Deep Learning-Based Mammogram Analyzer

Deep learning techniques utilize learning methods that allow a machine to be given a raw data and determine representations or features needed for data classification. Deep learning network involves numerous interconnected nodes referred to as neurons. Input neurons are activated by input data that activates other neurons in different layers of the network, based on the connection to other neurons which are governed by machine parameters called weights. A neural network behaves in certain manner based on its weights and interconnections. Learning refines the machine parameters called weights and thus the connection between the neurons in the network such that it gives the desired output. The machine parameters or weights in the network are adjusted by a back-propagation algorithm based on learning. The back-propagation algorithm continually adjusts the weights such that the "loss function" is minimum for all learning data sets or training data sets as it is also sometimes called in the literature. The "loss function" is the difference between the desired and the actual output of the neural network for a given learning or training data. The loss function is minimized for all learning or training data sets and the weights are adjusted accordingly. There are many different back-propagation algorithms used in the design of deep learning networks.

Deep learning operates on the understanding that many datasets include features that can be resolved into hierarchy of features from higher level to lower level. In the case of image analysis, for example, rather than looking for the object in the image, it is more efficient to look for edges and an edge has various details of resolution, low level to the high level. The hierarchical layers of a deep neural network, each represents a different level of details of edge, starting from the low level to the high level.

There are various types of deep learning networks: Feedforward neural network, radial basis function neural network, multilayer perception, convolutional neural network (CNN), Recurrent neural network (RNN), modular neural network, and Sequence to Sequence model network. Convolutional neural networks are biologically inspired in that the connectivity pattern of neurons resembles the organization of animal visual cortex. The convolutional neural network has several variations that are used to locate multiple objects in an image, which are applicable in locating multiple cancer locations in a breast image. Object detection is the process of finding and classifying objects in an image. The regions with convolutional neural network (R-CNN) combines rectangular region proposals with convolutional neural network features. R-CNN is a two-stage detection algorithm. The first stage identifies a subset of regions in an image that might contain an object. The second stage classifies the object in each region. The other variations of R-CNN, Fast R-CNN and Faster R-CNN have increasing computational speed. The other algorithm that is popular is You Only Look Once (YOLO) for real time object detection and classification with incredible speed but it has difficulties in detecting smaller objects.

An example where deep learning technique is used in medical field is mammography. Mammography is used to screen for breast cancer and other breast abnormalities. Traditionally, mammogram was done using X-ray films, however recently digital X-ray imaging is used to capture the breast images. The digital images facilitate easy storage and analysis. Digital images make easier way for applying Deep Learning models for assessment and prediction of cancer. Three-dimensional (3D) mammogram is the latest development in mammography and is also referred to as digital breast tomosynthesis (DBT). Two-dimensional mammography is a full-field digital mammography, and synthetic 2D mammography produces 2D pictures derived from 3D data produced by DBT by combining various enhanced sliced of DBT. Breast tomosynthesis reconstructs a 3D image out of various 2D images obtained as a series of projected X-ray images obtained by angular displacement of an X-ray source.

Another modality for breast imaging is ultrasound. Ultrasound is a high frequency sound wave; the reflected sound waves containing information on the depth, kind of tissue or fluid are collected, and an image is reconstructed. Ultrasound imaging of the breast is used when the breast density is high and the breast is filled with glandular and connective tissue and less fatty muscles, that makes it difficult to see the tumor in an X-ray or an magnetic resonance image (MRI). These ultrasound images can also be used with Deep Learning models to predict breast cancer.

Yet another modality for breast imaging is magnetic resonance imaging (MRI). MRI uses magnetic waves to produce images of the internal organs. Breast MRI produces images of breast tissue by detecting movements of atoms within the body which can reveal information about the abnormalities of the breast. Deep learning models can also be used on the MRI images to classify the images as cancer or benign.

Figure 4:
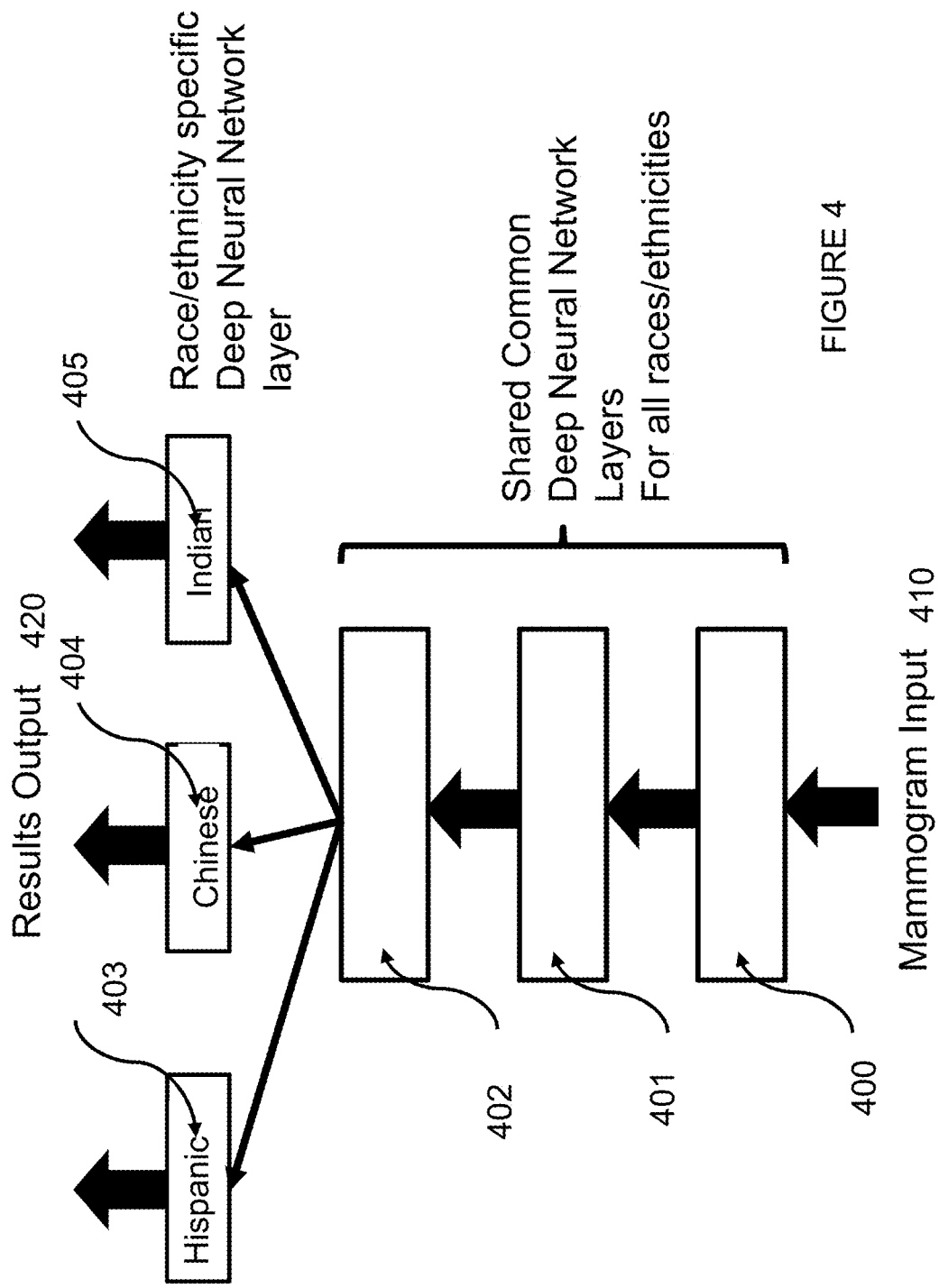
FIG. 4 shows a CNN processor containing layers that are common for all races and groups, and layers specialized specific to a particular group or race.

FIG. 4 is one of the embodiments of our system. Layers 400-402 are hidden layers in a convolutional neural network that contain the edge details of a breast image in the increasing order of details. Layer 401 contains the coarse details whereas layer 402 contains the finer details. Instead of three layers of this section of the hidden layers of CNN, it can be tens or hundreds or even thousands of layers. These layers are common layers for all races and these layers were obtained by training large labeled data of breast images of both cancerous and non-cancerous types. Upper layers denoted by 403-405 are race specific layers, where for example layer 403 is obtained by training the breast images of only Hispanic patients, layer 404 by training the breast images of only Chinese patients, and layer 405 is a layer obtained by training the breast images of only Indian patients. Layers 403-405 can be extended to represent many different ethnic, racial, or other groups that have inherently different physical features.

Other races or ethnicities include White, Caucasian, Caucasoid (as used in academia), Black, Negroid (as used in academia), African, African American, Asian, Asian American, East Asians, Korean, Japanese, Taiwanese, Southeast Asians, South Asians, Mongoloid (as used in academia), Indonesians, Native American, Pacific Islanders, Mixed Races or Multiracial Americans, Mestizo, Mulatto, European Americans, Middle Eastern, White Hispanics, Latinos, Non-Hispanic White, American Indians, Alaska Natives, Native Hawaiian, American Samoans, and others. Each of these or any combinations of these can be grouped as a race-specific layer.

Layers 400-402 are shared layers that can be hidden layers of CNN, R-CNN, Fast R-CNN, or Faster R-CNN. Layer 400 interfaces with the mammogram input and layers 403-405 interface with the output layer of the network.

Models of a convolutional neural network can be trained using traditional centralized machine learning techniques. Further, the models can also be trained using federated learning (also known as collaborative learning). Federated learning is a machine learning technique that trains an algorithm across multiple decentralized edge devices or servers holding local data samples, without exchanging them. This approach stands in contrast to traditional centralized machine learning techniques where all the local datasets are uploaded to one server, as well as to more classical decentralized approaches which often assume that local data samples are identically distributed.

Federated learning enables multiple actors to build a common, robust machine learning model without sharing data, thus allowing to address critical issues such as data privacy, data security, data access rights and access to heterogeneous data.

Some implementations of federated learning include centralized federated learning, decentralized federated learning, and heterogeneous federated learning. Federated learning can include iterative learning.

Federated learning aims at training a machine learning algorithm, for instance deep neural networks, on multiple local datasets contained in local nodes without explicitly exchanging data samples. The general principle consists in training local models on local data samples and exchanging parameters (e.g., the weights and biases of a deep neural network) between these local nodes at some frequency to generate a global model shared by all nodes.

The main difference between federated learning and distributed learning lies in the assumptions made on the properties of the local datasets, as distributed learning originally aims at parallelizing computing power where federated learning originally aims at training on heterogeneous datasets. While distributed learning also aims at training a single model on multiple servers, a common underlying assumption is that the local datasets are identically distributed (iid) and roughly have the same size. None of these hypotheses are made for federated learning; instead, the datasets are typically heterogeneous and their sizes may span several orders of magnitude.

Models of a convolutional neural network can be trained by active learning. Active learning is a special case of machine learning in which a learning algorithm can interactively query a user (or some other information source) to label new data points with the desired outputs. The information source can be referred to as a teacher or oracle.

There are situations in which unlabeled data is abundant but manual labeling is expensive. In such a scenario, learning algorithms can actively query the user or teacher for labels. This type of iterative supervised learning is called active learning. Since the learner chooses the examples, the number of examples to learn a concept can often be much lower than the number required in normal supervised learning.

With this approach, there is a risk that the algorithm is overwhelmed by uninformative examples. Recent developments are dedicated to multilabel active learning, hybrid active learning, and active learning in a single-pass (online) context, combining concepts from the field of machine learning (e.g., conflict and ignorance) with adaptive, incremental learning policies in the field of online machine learning.

Figure 5:
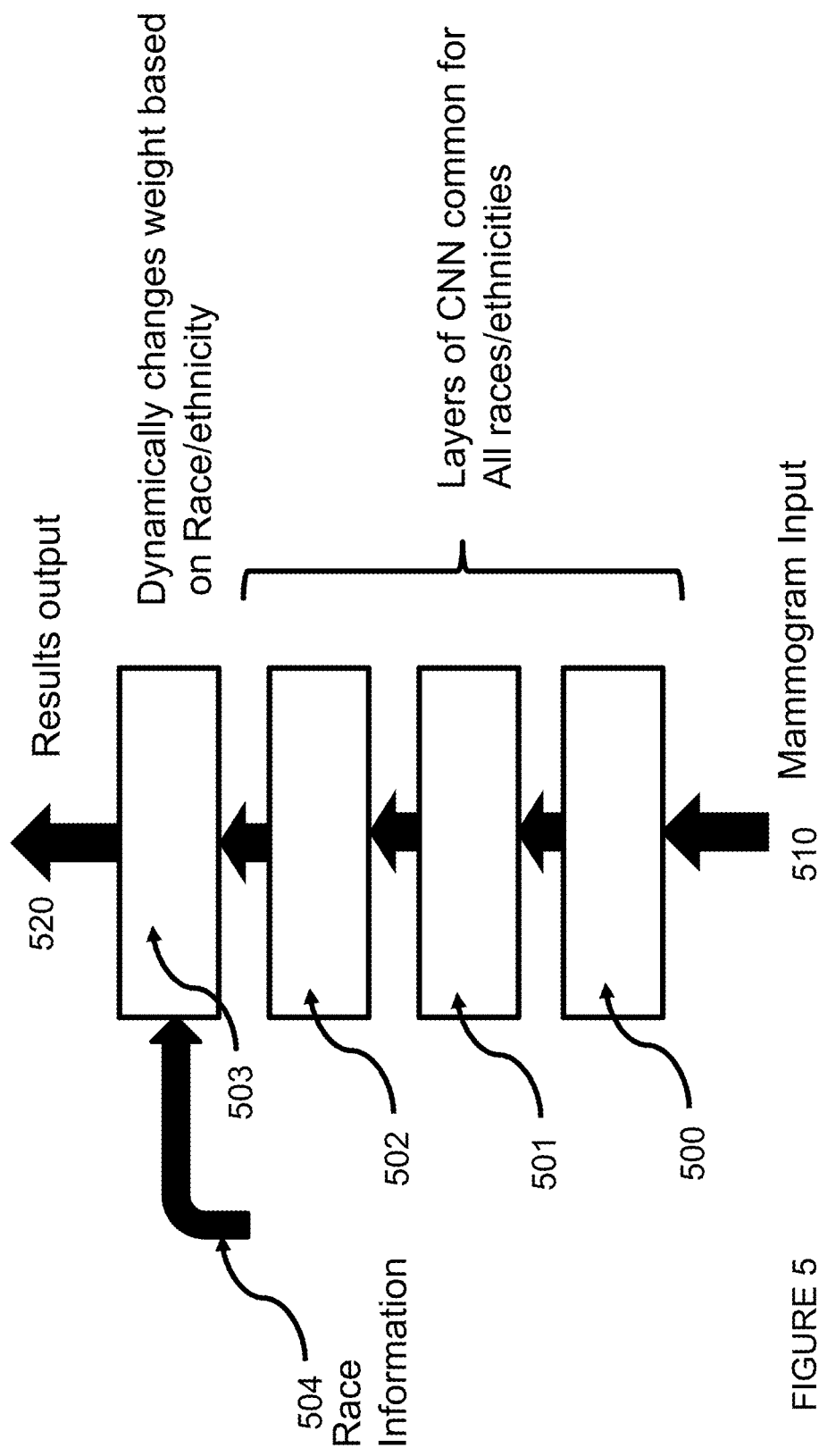
FIG. 5 shows a CNN processor containing layers that are common for all races and groups, and a dynamically changing specialized layer specific to a particular group or race.

Another embodiment of our system is described in FIG. 5. In this embodiment, the shared layers 500-502 are the same as layers 400-402 of the previous embodiment but the layers 403-405 of the previous embodiment are replaced by a single layer 503 whose weights will change dynamically according to the race information. The race information is either explicitly provided or automatically determined by a "race indicator algorithm" described in FIG. 6 below.

Figure 6:
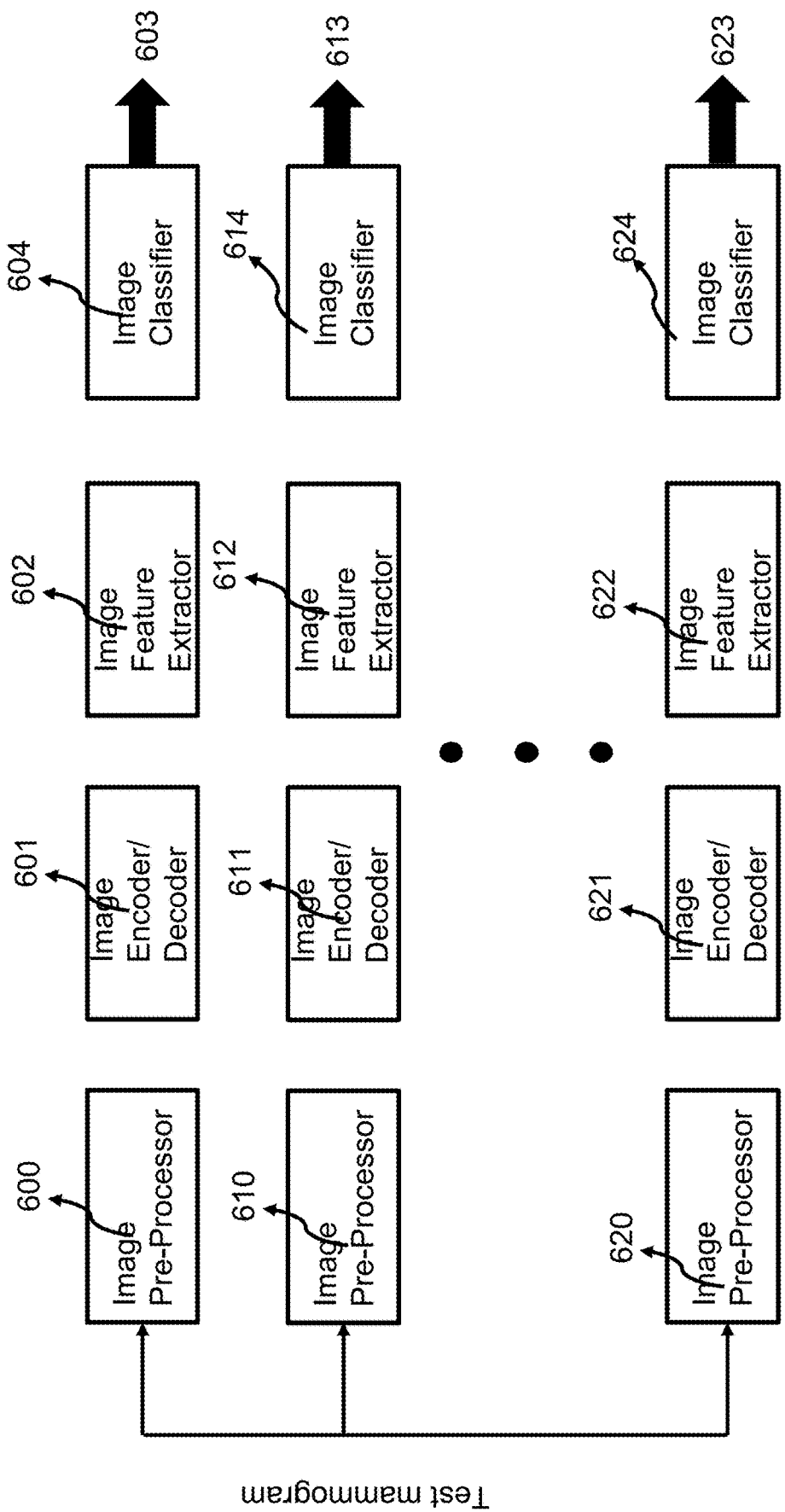
FIG. 6 shows a processor for race indication running algorithm made up of different variable autoencoders representing different races.

The race indicator algorithm shown in FIG. 6 has two primary components of the network: the autoencoder and the scorer. The autoencoder 601, 611, 621 is the component which learns what a mammogram of a particular race looks like whereas the scorer 603, 613, 623 scores how closely a given image of a mammogram fits the model of a race captured by the autoencoder. That is, the autoencoder has been trained for encoding and decoding mammograms of a particular race and in that sense knows what a mammogram of a particular race looks like, whereas the scorer doesn't know anything about race of the mammograms but simply judges the quality of the encoding or decoding process. Although both of these components could be developed as neural networks, only the autoencoder was developed as a neural network for the embodiment described here. The autoencoder is a variational autoencoder and the scorer utilizes a one-class SVM 604, 614, 624 which classifies each autoencoding as effective or ineffective. Due to the nature of these components, images from each race were necessary in training the system.

In more detail, the race indicator can be represented in five steps: (1) normalize the mammogram orientation, (2) encode or decode the mammogram, (3) threshold the original and decoded mammograms, (4) calculate the MSE pixel difference between the original and decoded mammograms, and (5) pass 1 minus the MSE values to a one-class SVM.

The first step, normalizing mammogram orientation, reduces the burden on the autoencoder without affecting overall system performance. To normalize orientation, each input image is multiplied, pixel-by-pixel, by an image that is black on the left side and white on the right side and an image that is white on the left side and black on the right side. Next, the pixel by-pixel multiplications are summed for the black-on-left and black-on right image cases to produce two results. The input image is flipped if and only if the black-on-left, white-on-right multiplication produces the highest result.

In the second step, the orientation-normalized image is first encoded, compressed, and then decoded, uncompressed, by a variational autoencoder. If the input image is a mammogram of the same race, the autoencoder will do a decent job encoding or decoding but if the input image is not a mammogram of the same race, the autoencoder will do a very poor job.

In the third step, the original and autoencoded images are thresholded. Thresholding is an unsupervised clustering technique by which lighter pixels are saturated to the highest possible value and darker pixels are floored to 0. The threshold is image dependent and is calculated as the average of cluster means from a 2-means clustering algorithm.

In the fourth step, the original and autoencoded images are compared via pixel-by-pixel mean squared error (MSE). This MSE operation is performed for both thresholded and non-thresholded pairs of images and can be written as 1−mean ((x0−x1)^2) where x0 and x1 represent pixel value arrays of the two images being compared.

In the fifth and final step, one minus each of the two MSE values is passed to a one-class SVM which declares the autoencoding to be effective or ineffective and produces a final label of mammogram of the race indicated by the autoencoder model or not.

Out of these five steps, the variational autoencoder is perhaps the most complex. An autoencoder is a neural network that attempts to encode or compress an input into a minimal number of values and then decode or uncompress these values to reproduce the original input. A variational autoencoder is a type of autoencoder where the input is compressed into a set of mean and standard deviation values. These mean and standard deviation values are used to modify samples drawn from a normal distribution, and these modified samples are fed into the decoder to reconstruct the original input. For the variational autoencoder used in this study, a convolutional neural network layer followed by four fully connected layers is used to encode each input image into two mean and two standard deviation values. Four fully connected decoder layers are then used to recreate the input image. The encoder layers are progressively smaller while the decoder layers are progressively larger-exact layer sizes can be seen in FIG. 4. The autoencoders used in the described example can also be replaced by generative adversarial networks (GANs).

Figure 7:
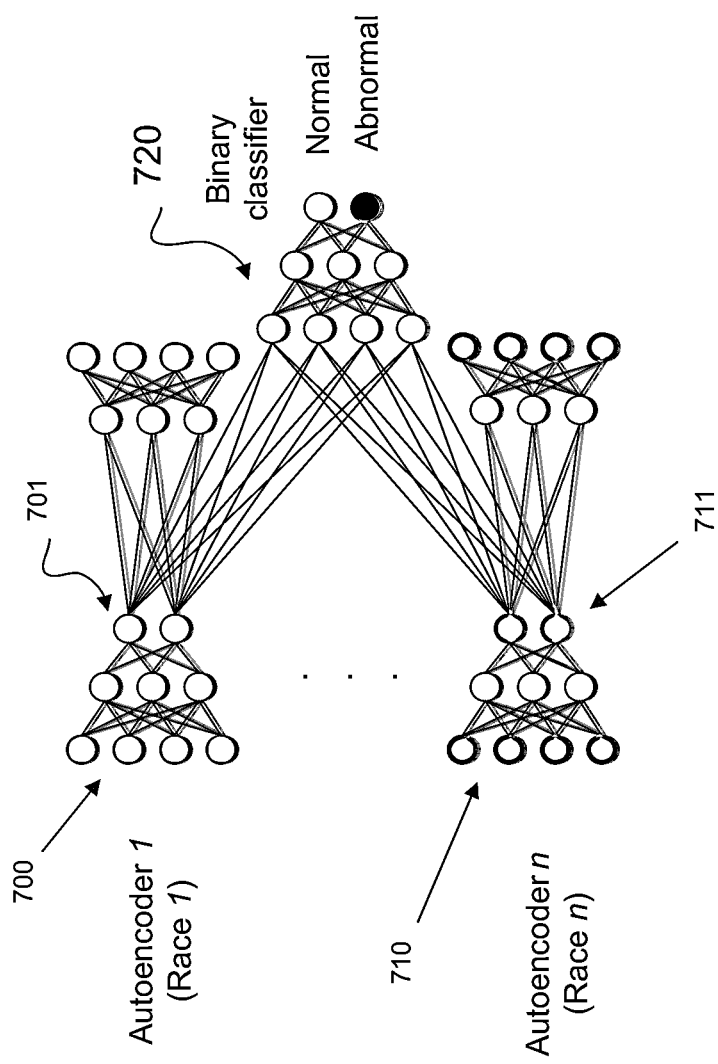
FIG. 7 shows a processor running deep neural network algorithm made up of autoencoders representing different races and a classifier for analysis of mammograms.

FIG. 7 shows a third embodiment of our system. It consists of variational autoencoders 700-710 trained in mammograms of each race or group, all placed in parallel and the hidden layers 701-711 of the autoencoders that contain the compact information about the respective race or group are connected together to form another deep learning network 720 that is trained to discriminate between a normal or abnormal mammogram. The binary classifier can be replaced by a multiclass classifier, for example a three-class classifier can be used to classify mammograms as normal, benign, or malignant.

Apart from detecting accurately whether the mammogram is normal or abnormal, the same deep neural network can also be used to predict the beast density. Typically, fatty breasts are at less risk for cancer while dense breasts are at greater risk. The Breast Imaging and Reporting Data System (BI-RADS) categorizes breasts into four density classes: fatty, sparsely dense, heterogeneously dense, and extremely dense. Sometimes, density will be discussed with binary labels of low density (fatty or sparsely dense) and high density (heterogeneously and extremely dense).

Figure 8:
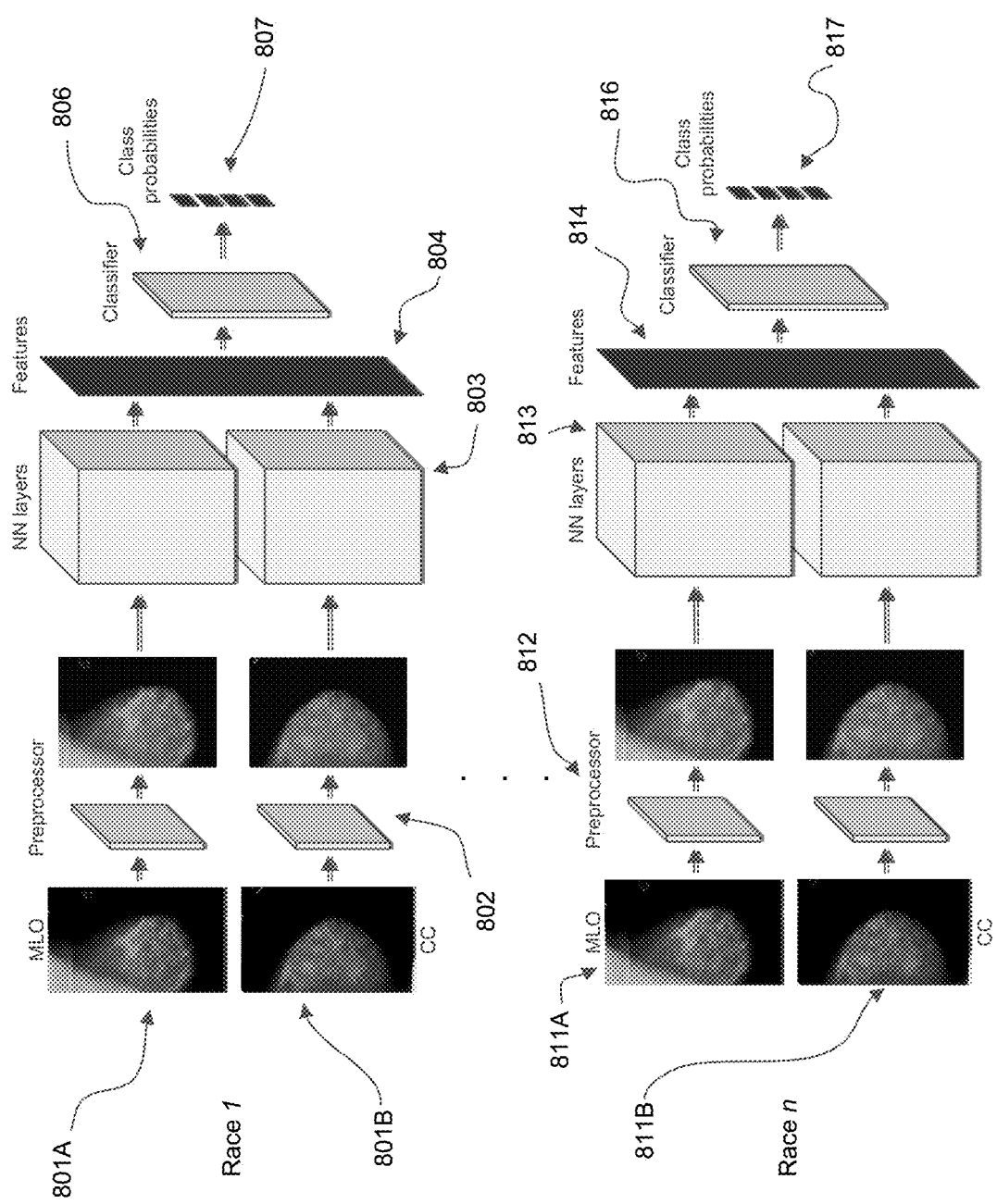
FIG. 8 shows a system running algorithm for breast density prediction of different races.

FIG. 8 shows a network architecture which can be referred as DualViewNet to perform joint classification on mediolateral oblique (MLO) 801A, 811A and craniocaudal (CC) 801B, 811B mammograms corresponding to the same breast. The MLO view is easier to classify than the CC view, and we have shown that a network which considers both views simultaneously will have more accuracy on a breast-by-breast basis than a network which considers only one view at a time. Our network accepts only MLO and CC views for a single breast rather than MLO and CC views for both breasts from a single woman. DualViewNet passes the MLO and CC mammograms to two separate convolutional layers based on MobileNetV2, although convolutional layers from any state-of-the-art image classifier could be used. Two sets of features output from the convolutional layers are then concatenated and passed into a classifier which outputs probabilities for each of the density classes.

Now, to create a deep learning network to predict breast density for different races, the embodiments described before if FIGS. 4-7 can be modified as follows. In the embodiment of FIG. 4, layers 401, 404, are replaced respectively by layers 804 and 814. Similarly, in the embodiment of FIG. 5, layers 503 will be replaced by layers 804 or 814 depending on the race indicator value. In the embodiment of FIG. 6, layers 602 and 612 are replaced by layers 804 and 814, respectively. And in the embodiment of FIG. 7, layers 701 and 711 are respectively replaced by layers 804 and 814.

Overall, the system takes in mammogram images and outputs the malignance score of the image and bounding boxes around the regions of malignant and benign tumors. The mammogram images are mapped from grayscale to RGB (red-green-blue) space via a sequential color mapping scheme. The first reason for this mapping is that color mapping can enhance the visual dynamic range of an image. By utilizing the entire RGB space, images can convey greater visual information about relative intensities than can be done using grayscale. The second reason for this mapping is because the mammograms were converted to 24-bit RGB JPEG images for input into the network. Mammograms may be up to 12-bit or 16-bit grayscale, and mapping from 16-bit grayscale to grayscale in 24-bit RGB space requires truncation of bits. That is, 24-bit RGB space can only represent 8-bit grayscale. By color mapping mammograms, relative pixel intensities can be represented by more than 8-bits in 24-bit RGB space. Therefore, more information regarding relative pixel values is maintained through color mapping. Although there are many different color map choices, a sequential color mapping scheme is used because it causes pixel lightness to increase with pixel value and is thereby visually intuitive. For example, low pixel values will map to a dark red while high pixel values will map to a light yellow. In addition to color mapping, contrast limited adaptive histogram equalization (CLAHE) is used to improve mammogram quality by enhancing image contrast. CLAHE enhances image contrast by equalizing pixel value distributions. In other words, CLAHE will make dark pixels darker and light pixels lighter such that the dynamic pixel range is more fully leveraged. In the case of mammograms, CLAHE can enhance the visibility of edges and features critical for identifying tumors. Oftentimes, breast tissue pixels are clustered and potentially saturated in the highest range of possible pixel values. By equalizing the range of these tissue pixels, pertinent tissue features become easier to identify.

The image is input to a machine learning algorithm. There are many types of machine learning algorithms such as Support Vector Machines (SVM) and Deep Neural Networks that can be used. We used Convolutional Neural Network (CNN), a type of Deep Neural Network.

The CNN has three main types of layers, which are: (1) Convolutional layer (2) Pooling layer and (3) Fully-connected (FC) layer. The convolutional layer is the first layer of a convolutional network, it is normally passed through a activation function. While convolutional layers can be followed by additional convolutional layers or pooling layers, the fully-connected layer is the final layer. With each layer, the CNN increases in its complexity, identifying greater portions of the image. Earlier layers focus on simple features, such as lines and edges. As the image data progresses through the layers of the CNN, it starts to recognize larger elements or shapes of the object until it finally identifies the intended objects which are benign and malignant breast tumors in our case. The convolutional layer is the core building block of a CNN, and it is where most of the computation occurs. It requires a few components, which are input data, the mammogram in our case, a filter, and a feature map. This means that the input will have three dimensions—a height, width, and depth—which correspond to RGB equivalent of gray scale in a mammogram.

We also have a feature detector, also known as a kernel or a filter, which will move across the receptive fields of the image, checking if the feature is present. This process is known as a convolution. The feature detector is a two-dimensional (2-D) array of weights, which represents part of the image. While they can vary in size, the filter size is typically a 3×3 matrix; this also determines the size of the receptive field. The filter is then applied to an area of the image, and a dot product is calculated between the input pixels and the filter. This dot product is then fed into an output array. Afterwards, the filter shifts by a stride, repeating the process until the kernel has swept across the entire image. The final output from the series of dot products from the input and the filter is known as a feature map. Each output value in the feature map does not have to connect to each pixel value in the input image. It only needs to connect to the receptive field, where the filter is being applied. The weights in the feature detector remain fixed as it moves across the image, which is also known as parameter sharing. Some parameters, like the weight values, adjust during training through the process of backpropagation and gradient descent. However, there are three hyperparameters which affect the volume size of the output that need to be set before the training of the neural network begins. These include:

1. The number of filters affects the depth of the output. For example, three distinct filters would yield three different feature maps, creating a depth of three.

2. Stride is the distance, or number of pixels, that the kernel moves over the input matrix. While stride values of two or greater is rare, a larger stride yields a smaller output.

3. Zero-padding is usually used when the filters do not fit the input image. This sets all elements that fall outside of the input matrix to zero, producing a larger or equally sized output.

After each convolution operation, a CNN applies a Rectified Linear Unit (ReLU) transformation to the feature map, introducing nonlinearity to the model. Another convolution layer can follow the initial convolution layer. When this happens, the structure of the CNN can become hierarchical as the later layers can see the pixels within the receptive fields of prior layers. Ultimately, the convolutional layer converts the image into numerical values, allowing the neural network to interpret and extract relevant patterns.

Pooling layers, also known as down sampling, conducts dimensionality reduction, reducing the number of parameters in the input. Like the convolutional layer, the pooling operation sweeps a filter across the entire input, but the difference is that this filter does not have any weights. Instead, the kernel applies an aggregation function to the values within the receptive field, populating the output array. There are two main types of pooling: Max pooling and Average pooling. Max pooling selects the pixel with the maximum value to send it to the output array and the average pooling calculates average value within the receptive field to send it to the output array. While a lot of information is lost in the pooling layer, it also has several benefits to the CNN. They help to reduce complexity, improve efficiency, and limit risk of overfitting. We use Max pooling in our system.

After learning features in many layers, the architecture of the CNN shifts to classification. The classification layers consist of an input layer followed by many hidden layers and an output layer. The next-to-last layer is a fully connected layer that outputs a vector of k dimensions, where k is the number of classes that the network will predict. In our case it is 2 or 3 depending on the embodiment. In the fully-connected layer, each node in the output layer connects directly to a node in the previous layer. This layer performs the task of classification based on the features extracted through the previous layers and their different filters. While convolutional and pooling layers tend to use ReLu functions, fully-connected layers usually leverage a softmax activation function to classify inputs appropriately, producing a probability from 0 to 1.

The CNN which is a kind of Deep Neural Network (DNN) is in general made up of feature learning layers and classification layers. The classification layers consist of an input layer followed by n hidden layers and an output layer. Each of the layers is made up of artificial neurons defined by many inputs and one output. The inputs are number and each of them is associated with a weight. The artificial neuron computes a weighted sum of its inputs (where x are inputs and w are weights associated with the inputs.) and applies a activation function. The activation function can be such as a simple step function, a hyperbolic tangent function, a ReLU function or a Logit function. In statistics, the logit function is the quantile function associated with the standard logistic distribution. We have used ReLU function in our DNN. Every layer except the last layer includes a bias to the artificial neuron which is fully connected to the next layer. Building a machine learning model boils down to computing the weights of the DNN such that the prediction error which is the difference between what is predicted by the model and what is the target label for the sample data is minimum. This error should be minimum for any generalized data. This is achieved by training the DNN with known data. For each training instant the backpropagation algorithm first makes a prediction using forward pass and measuring the error, then goes through each layer in reverse to measure the error contribution from each connection via reverse pass, and finally tweaks the connection weights to reduce the error. This optimization is done using Gradient Descent Algorithm.

We used mammogram data from U.S., India, Taiwan, South America, Sub-Saharan Africa, and Middle East for training. The mammograms were annotated by U.S. board certified mammographers. These annotations were supported by ground truth provided by pathology and radiology reports of the patients.

The CNN is made up of FIG. 4 is one of the embodiments of our system, 400-402 are hidden layers in a convolutional neural network that contains the edge details of a breast image in the increasing order of details. Layer 401 contains the coarse details whereas layer 402 contains the finer details. Instead of three layers of this section of the hidden layers of CNN, it can be tens or hundreds or even thousands of layers. These layers are common layers for all races and these layers were obtained by training large, labeled data of breast images of both cancerous and non-cancerous types. Upper layers denoted by 403-405 are race specific layers, where for example layer 403 is obtained by training the breast images of only Hispanic patients, layer 404 by training the breast images of only Chinese patients, and layer 405 is a layer obtained by training the breast images of only Indian patients. Layers 403-405 can be extended to represent many different ethnic, racial, or other groups that have inherently different physical features.

Layers 400-402 are shared layers that can be hidden layers of CNN, R-CNN, Fast R-CNN, or Faster R-CNN. 400 interfaces with the mammogram input and layers 403-405 interface with the output layer of the network.

Another embodiment of our system is described in FIG. 5. In this embodiment, the shared layers 500-502 are the same as layers 400-402 of the previous embodiment but the layers 403-405 of the previous embodiment are replaced by a single layer 503 whose weights will change dynamically according to the race information. The race information is either explicitly provided or automatically determined by a "race indicator algorithm" described in FIG. 6.

In FIGS. 6 and 7, autoencoders are artificial neural networks capable of learning efficient representation of input data called "codings" without any supervised learning, and then learn to reconstruct the data back from the reduced encoded representation called "bottleneck" to representation that is close to the original input as possible called "decodings." The "bottleneck" or the compressed data is the byproduct of the autoencoder's attempt to learn the identity function under some constraints. The architecture of the autoencoders can be divided into three different components: the encoder, the bottleneck, and the decoder. The architecture of an autoencoder is a feed-forward architecture, with a structure much like a single layer perceptron used in multilayer perceptrons. Much like regular feed-forward neural networks, the autoencoder is trained using backpropagation.

The encoder component of the autoencoder is typically a feed forward, densely connected Deep Neural Network. The purpose of the encoding layers is to take the input data and compress it into a latent space representation, generating a new representation of the data that has reduced dimensionality. The bottleneck layers deal with the compressed representation of the data. The bottleneck code is carefully designed to determine the most relevant portions of the observed data, or the features of the data that are most important for data reconstruction. The goal here is to determine which aspects of the data need to be preserved and which can be discarded. The bottleneck code needs to balance two different considerations: representation size and feature relevance. The bottleneck performs element-wise activation on the weights and biases of the network. The bottleneck layer is also sometimes called a latent representation or latent variables The decoder layer is what is responsible for taking the compressed data and converting it back into a representation with the same dimensions as the original. The conversion is done with the latent space representation that was created by the encoder. Autoencoders learn automatically. They do not require labels, and if given enough data it is relatively easy to get an autoencoder to reach high performance on a specific kind of input data. When designing an autoencoders, one need to pay attention to four different model hyperparameters: code size, layer number, nodes per layer, and loss function. The code size decides how many nodes begin the middle portion of the network, and the fewer nodes that compress the data more. In a DNN based autoencoder, while the number of layers can be any number that is appropriate, the number of nodes in a layer should decrease as the encoder goes on. Meanwhile, the opposite holds true in the decoder, meaning the number of nodes per layer should increase as the decoder layers approach the final layer. Finally, the loss function of an autoencoder is typically either binary cross-entropy or mean squared error. Mean squared error is used in our design.

There are various types of autoencoders. Denoising autoencoder, Sparse autoencoder and variational encoders are some of them. Variational encoders are used in the embodiment 3. A variational autoencoder produces a probability distribution for the different features of the training images or the latent attributes. When training, the encoder creates latent distributions for the different features of the input images. Because the model learns the features or images as Gaussian distributions instead of discrete values, it is capable of being used to generate new images. The Gaussian distribution is sampled to create a vector, which is fed into the decoding network, which renders an image based on this vector of samples. Essentially, the model learns common features of the training images and assigns them some probability that they will occur. The probability distribution can then be used to reverse engineer an image, generating new images that resemble the original, training images. When training the network, the encoded data is analyzed and the recognition model outputs two vectors, drawing out the mean and standard deviation of the images. A distribution is created based on these values. This is done for the different latent states. The decoder then takes random samples from the corresponding distribution and uses them to reconstruct the initial inputs to the network.

In FIG. 8, we present a network architecture which we call DualViewNet to perform joint classification on mediolateral oblique (MLO) 501A, 511A and craniocaudal (CC) 501B, 511B mammograms corresponding to the same breast. The MLO view is easier to classify than the CC view, and we have shown that a network which considers both views simultaneously will have more accuracy on a breast-by-breast basis than a network which considers only one view at a time. Our network accepts only MLO and CC views for a single breast rather than MLO and CC views for both breasts from a single woman.

We applied a series of preprocessing techniques to the mammograms prior to training and testing. For both training and testing, mammograms were color mapped from 16-bit grayscale to 24-bit RGB via the magma color mapping scheme. For validation and testing, images were then resized and center cropped to 336×224. MobileNetV2 was pretrained on 224×224 images, but we used an input size of 336×224 to accommodate the typical aspect ratio of mammograms. For training, images were cropped to a random size and aspect ratio, resized to 336×224 and then randomly flipped horizontally to provide dataset augmentation for reducing overfit. Lastly, mammograms pixel values were normalized to a mean of [0.485, 0.456, 0.406] and standard deviation of [0.229, 0.224, 0.225] as was done during pretraining.

The algorithm first passes the MLO and CC mammograms through a preprocessing stage as indicated by numbers 802 and 812 in FIG. 8. MLO and CC mammograms are indicated by numbers 801A and 801B as well as 811A and 811B. The algorithm then passes the MLO and CC mammograms to separate convolutional layers based on MobileNetV2, although convolutional layers from any state-of-the-art image classifier could be used. These convolutional layers are indicated by numbers 803 and 813. Two sets of features output from the convolutional layers are then concatenated and passed into a classifier which outputs probabilities for each of the density classes. The concatenated features are indicated by numbers 804 and 814, the classifier is indicated by numbers 806 and 816, and output probabilities are indicated by numbers 807 and 817.

In an implementation, a system for analyzing mammograms includes a deep neural network (DNN) with multiple layers representing features of mammograms of general population (e.g., multiple ethnicities or races); and a final layer of the DNN representing the features of a specific race (e.g., only a single ethnicity or race). Instead of a single final layer, there can be s multiple final layers of DNN to represent the mammogram features of specific races, such as each final layer representing a different single ethnicity or race.

The final layer or layers can be trained with data comprised, for example, of only Caucasian ethnicity, only African ethnicity, only Hispanic ethnicity, only Indian ethnicity, only Chinese ethnicity, only Middle Eastern ethnicity, or only Native American ethnicity. The final layers of DNN containing the features of race specific mammogram information can dynamically change according to the race information provided explicitly.

The layers of DNN containing the features of race specific mammogram information can be provided by the hidden layer of a variational autoencoder. The final layer of the DNN representing the features of a specific race can be replaced by multiplicity of layers of DNN representing the features of a specific race.

The DNN can be trained by machine learning. The DNN can be trained by federated learning. The final layer or layers can be trained using machine learning. The final layer or layers can be trained using active learning In an implementation, a system for analyzing mammograms includes: a convolutional neural network (CNN) with multiple layers representing features of mammograms of general population; and a final layer of the CNN representing the features of a specific race. The multiple final layers of CNN can represent the mammogram features of a specific race.

The final layer or layers are trained with data comprised of only Caucasian ethnicity, only African ethnicity, only Hispanic ethnicity, only Indian ethnicity, only Chinese ethnicity, only Middle Eastern ethnicity, or only Native American ethnicity. The final layers of CNN containing the features of race specific mammogram information can dynamically change according to the race information provided explicitly.

The layers of CNN containing the features of race specific mammogram information can be provided by the hidden layer of a variational autoencoder. The final layer of the CNN representing the features of a specific race can be replaced by multiplicity of layers of CNN representing the features of a specific race.

The CNN can be trained by machine learning. The CNN can be trained by federated learning. The final layer or layers can be trained using machine learning. The final layer or layers can be trained using active learning.

In an implementation, a system includes a neural network (e.g., deep neural network or convolutional neural network) including a number of layers; a first set of layers of the neural network includes a first model trained by machine learning using a first set of training data comprising first mammogram images from multiple ethnicities; and a second set of layers of the neural network includes a second model trained by machine learning using a second set of training data comprising second mammogram images from only a single ethnicity. The second set of layers of deep neural network is trained with data comprised of only Caucasian ethnicity, only African ethnicity, only Hispanic ethnicity, only Indian ethnicity, only Chinese ethnicity, only Middle Eastern ethnicity, or only Native American ethnicity.

An input mammogram image is to be analyzed by the neural network. The input mammogram image is evaluated by the first model and a first determination is made of a cancer diagnosis or no cancer diagnosis. The input mammogram image is evaluated by the second model wherein the second model is sifted through all the ethnicities and a multiple determination of a cancer diagnosis or no cancer diagnosis is made. Based on a polling of results of evaluations made by first and multiplicity of second models, when the majority determination (e.g., greater than 50 percent) is a cancer diagnosis, designating an outcome of the neural network as being a cancer, otherwise designating the outcome of the neural network as being no cancer. For example, for a majority determination of three models, two or more having the same result will be the majority determination.

The first set of layers of neural network comprising a first model trained by federated learning. The second set of layers can be trained by active learning. The first mammogram images is at least one of X-ray imagery, magnetic resonance imagery, ultrasound image, computer tomography imagery, or a combination.

In an implementation, a system for predicting breast density includes a deep neural network (DNN) with multiple layers representing features of mammograms of general population; and a final layer of the DNN representing the features of a specific race. There can be multiple final layers of DNN where each represents the mammogram features of a specific race given by a variational auto encoder.

The final layers of DNN containing the features of race specific mammogram information can dynamically change according to the race information provided explicitly. The layers of DNN containing the features of race specific mammogram information can be provided by the hidden layer of a variational auto encoder. The layers of DNN can be (or be replaced) by a convolutional neural network (CNN). The DNN with multiple layers representing the features of mammograms of general population can be learned through federated learning.

The final layers of the DNN can be replaced by multiplicity of layers. The final layer or layers of DNN can be learned through active learning.

In a implementation, a system includes a deep neural network (e.g., convolutional neural network) including a number of layers arranged in a hierarchy, where an input of the convolutional neural network is at a bottom of the hierarchy of layers and an output is at a top of the hierarchy of layers; a first number or set of layers of the convolutional neural network which is trained by federated learning (or other machine learning, but not active learning) using a first set of training data including first breast images including multiple ethnicities (e.g., representative of a general population of a place such as the United States); a second layer, trained by active learning (e.g., trained differently from that used for the first layers) using a second set of training data including second breast images from only a single ethnicity, a first ethnicity; and a third layer, trained by active learning using a third set of training data including third images from only a single ethnicity, a second ethnicity that is different from the first ethnicity, where the second and third layers are at the same level in the hierarchy of the convolutional neural network, and the second and third layers are above the first layers of the convolutional neural network.

The convolutional neural network including the first layers, second layer, and third layer provides a machine learning model. A breast image for analysis is input to the input of the convolutional neural network. The output of the convolutional neural network provides a diagnosis probability of breast cancer.

A fourth layer and fifth layer are within the first layers of the convolutional neural network. The fifth layer is above the fourth layer. The breast image for analysis is input to the fourth layer. The fourth layer extracts first different features in the breast image. The fifth layer stores first weightings for the first different features in the breast image extracted by the fourth layer. The first weightings for the first different features are input to the second and third layers. Given the first weightings from the fifth layer, the second layer outputs second weightings for second different features. Given the first weightings from the fifth layer, the third layer outputs third weightings for third different features.

The first weightings can correspond to a cancer diagnosis. In an implementation, the input the convolutional neural network does not include an identification of an ethnicity (which can be an optional input) of the breast image.

In an implementation, the breast image for analysis and an identification of an ethnicity of the breast image are input to the fourth layer. The fourth layer extracts first different features in the breast image. The fifth layer stores first weightings for the first different features in the breast image extracted by the fourth layer. When the ethnicity of the breast image for analysis is the first ethnicity, the first weightings for the first different features are input to the second layer, and given the first weightings from the fifth layer, the second layer outputs second weightings for second different features. When the ethnicity of the breast image for analysis is the second ethnicity, the first weightings for the first different features are input to the third layer, and given the first weightings from the fifth layer, the third layer outputs third weightings for third different features.

When the ethnicity of the breast image for analysis is first ethnicity, the first weightings for the first different features are not input to the third layer. When the ethnicity of the breast image for analysis is second ethnicity, the first weightings for the first different features are not input to the second layer.

When the ethnicity of the breast image for analysis is not the first ethnicity and not the second ethnicity, the first weightings for the first different features are input to the second the third layers. Given the first weightings from the fifth layer, the second layer outputs second weightings for second different features. And given the first weightings from the fifth layer, the third layer outputs third weightings for third different features.

Each of the first layers, second layer, and third layer has a single vote. A diagnosis probability of breast cancer is based on a majority of the votes, such that any two of the first layers, second layer, and third layer would constitute a majority.

The multiple ethnicities of the first layers may not include the first and second ethnicities. The multiple ethnicities of the first layers does not include at least one of the first ethnicity or second ethnicity. The first set of training data including first breast images, which do not include any of images from the third images or fourth images.

In a implementation, a system includes a deep neural network (e.g., convolutional neural network) including a number of layers arranged in a hierarchy, where an input of the convolutional neural network is at a bottom of the hierarchy of layers and an output is at a top of the hierarchy of layers; a first number or set of layers of the convolutional neural network which is trained by federated learning (or other machine learning, but not active learning) using a first set of training data including first breast images including multiple ethnicities (e.g., representative of a general population of a place such as the United States); a second layer, trained by active learning (e.g., trained differently from that used for the first layers) using a second set of training data including second breast images from only a single ethnicity, a first ethnicity; and a third layer, trained by active learning using a third set of training data including third images from only a single ethnicity, a second ethnicity that is different from the first ethnicity, a fourth layer, trained by active learning using a fourth set of training data including fourth images from only a single ethnicity, a third ethnicity that is different from the first and second ethnicities, where the second, third, and fourth layers are at the same level in the hierarchy of the convolutional neural network, and the second, third, and fourth layers are above the first layers of the convolutional neural network.

Each of the first layers, second layer, third layer, and fourth layer can have a single vote. A diagnosis probability of breast cancer is based on a majority of the votes, such that any three of the first layers, second layer, third layer, and fourth layer would constitute a majority. And when there a majority of the votes is not obtained (e.g., 2-2 tie vote), the diagnosis probability of breast cancer is based on only the first layers, where the second, third, and fourth layers are not used in the diagnosis.

The convolutional neural network includes the first layers, second layer, third layer, and fourth layer providing a machine learning model. A breast image for analysis is input to the input of the convolutional neural network. The output of the convolutional neural network provides a diagnosis probability of breast cancer.

A fifth layer and sixth layer are within the first layers of the convolutional neural network, and the sixth layer is above the fifth layer. The breast image for analysis and an identification of an ethnicity of the breast image are input to the fifth layer, the fifth layer extracts first different features in the breast image. The sixth layer stores first weightings for the first different features in the breast image extracted by the fifth layer. When the ethnicity of the breast image for analysis is first ethnicity, the first weightings for the first different features are input to the second layer and not the third or fourth layers. Given the first weightings from the sixth layer, the second layer outputs second weightings for second different features.

In an implementation, a system includes a deep neural network (e.g., convolutional neural network) including a number of layers arranged in a hierarchy, where an input of the convolutional neural network is at a bottom of the hierarchy of layers and an output is at a top of the hierarchy of layers; a first number or set of layers of the convolutional neural network which is trained by federated learning (or other machine learning, but not active learning) using a first set of training data including first breast images including multiple ethnicities (e.g., representative of a general population of a place such as the United States); a second layer, trained by active learning (e.g., trained differently from that used for the first layers) using a second set of training data including second breast images from only a single ethnicity, a first ethnicity; and a third layer, trained by active learning using a third set of training data including third images from only a single ethnicity, a second ethnicity that is different from the first ethnicity, a fourth layer, trained by active learning using a fourth set of training data including fourth images from only a single ethnicity, and a third ethnicity that is different from the first and second ethnicities, where the second, third, and fourth layers are at the same level in the hierarchy of the convolutional neural network, and the second, third, and fourth layers are above the first layers of the convolutional neural network.

Each of the first layers, second layer, third layer, and fourth layer has a single vote, and a diagnosis probability of breast cancer is based on a majority of the votes such that any three of the first layers, second layer, third layer, and fourth layer would constitute a majority. When there a majority of the votes is not obtained, the diagnosis probability of breast cancer is based on only the first layers. A fifth layer and sixth layer are within the first layers of the convolutional neural network, and the sixth layer is above the fifth layer.

The breast image for analysis and an optional identification of an ethnicity of the breast image are input to the fifth layer, the fifth layer extracts first different features in the breast image, the sixth layer stores first weightings for the first different features in the breast image extracted by the fifth layer. When the ethnicity of the breast image for analysis is the first ethnicity, the first weightings for the first different features are input to the second layer and not the third or fourth layers. Given the first weightings from the sixth layer, the second layer outputs second weightings for second different features.

A fifth layer and sixth layer are within the first layers of the convolutional neural network, and the sixth layer is above the fifth layer. The breast image for analysis and is input to the fifth layer. The fifth layer extracts first different features in the breast image. The sixth layer stores first weightings for the first different features in the breast image extracted by the fifth layer.

When the ethnicity of the breast image for analysis is the first ethnicity, the first weightings for the first different features are input to the second layer and not the third or fourth layers. Given the first weightings from the sixth layer, the second layer outputs second weightings for second different features.

When the ethnicity of the breast image for analysis is the second ethnicity, the first weightings for the first different features are input to the third layer and not the second or fourth layers. Given the first weightings from the sixth layer, the third layer outputs third weightings for third different features, When the ethnicity of the breast image for analysis is the third ethnicity, the first weightings for the first different features are input to the fourth layer and not the second or third layers. Given the first weightings from the sixth layer, the fourth layer outputs fourth weightings for fourth different features.

When the ethnicity of the breast image for analysis is not identified, the first weightings for the first different features are input to the second, third, and fourth layers. Given the first weightings from the sixth layer, the second layer outputs second weightings for the second different features. Given the first weightings from the sixth layer, the third layer outputs third weightings for the third different features. Given the first weightings from the sixth layer, the fourth layer outputs fourth weightings for the fourth different features.

The first breast images includes at least one of mammograms, X-ray imagery, magnetic resonance imagery (MRI), computerized tomography (CT) scan imagery, ultrasound imagery, s sonography imagery, positron emission tomography (PET) imagery, or other imagery form other medical imaging technology.

The first set of training data can include ethnicity data for a general population (e.g., geographic area such as a country (U.S., China, or India), state (e.g., California, Texas, or Florida), region, (e.g., Europe, western U.S., or east coast), the second set of training data comprises ethnicity data for, as an example, a Hispanic ethnicity, the third set of training data comprises ethnicity data for, as an example, a Chinese ethnicity, and the fourth set of training data comprises ethnicity data for, as an example, an Indian ethnicity.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A system comprising:
    a convolutional neural network comprising a plurality of layers arranged in a hierarchy, wherein an input of the convolutional neural network is at a bottom of the hierarchy of layers and an output is at a top of the hierarchy of layers;
    a first plurality of layers of the convolutional neural network which is trained by federated learning using a first set of training data comprising first breast images comprising multiple ethnicities;
    a second layer, trained by active learning using a second set of training data comprising second breast images from only a single ethnicity, a first ethnicity;
    a third layer, trained by active learning using a third set of training data comprising third images from only a single ethnicity, a second ethnicity that is different from the first ethnicity; and
    a fourth layer, trained by active learning using a fourth set of training data comprising fourth images from only a single ethnicity, a third ethnicity that is different from the first and second ethnicities,
    wherein the second and third layers are at the same level in the hierarchy of the convolutional neural network, and the second and third layers are above the first layers of the convolutional neural network.

2. The system of claim 1 comprising:
    a fourth layer, trained by active learning using a fourth set of training data comprising fourth images from only a single ethnicity, a third ethnicity that is different from the first and second ethnicities.

3. The system of claim 1 wherein each of the first layers, second layer, and third layer has a single vote, and a diagnosis probability of breast cancer is based on a majority of the votes such that any three of the first layers, second layer, and third layer would constitute a majority, and
    when a majority of the votes is not obtained, the diagnosis probability of breast cancer is based on only the first layers.

4. The system of claim 3 wherein the convolutional neural network comprising the first layers, second layer, and third layer comprises a machine learning model,
    a breast image for analysis is input to the input of the convolutional neural network, and
    the output of the convolutional neural network provides a diagnosis probability of breast cancer.

5. The system of claim 4 wherein a fourth layer and fifth layer are within the first layers of the convolutional neural network, and the fifth layer is above the fourth layer, the breast image for analysis and an identification of an ethnicity of the breast image are input to the fourth layer, the fourth layer extracts first different features in the breast image, the fifth layer stores first weightings for the first different features in the breast image extracted by the fourth layer, when the ethnicity of the breast image for analysis is the first ethnicity, the first weightings for the first different features are input to the second layer and not the third layer, and given the first weightings from the fifth layer, the second layer outputs second weightings for second different features.

6. A system comprising:
a convolutional neural network comprising a plurality of layers arranged in a hierarchy, wherein an input of the convolutional neural network is at a bottom of the hierarchy of layers and an output is at a top of the hierarchy of layers;
a first plurality of layers of the convolutional neural network which is trained by machine learning and not active learning using a first set of training data comprising first breast images comprising multiple ethnicities;
a second layer, trained by active learning using a second set of training data comprising second breast images from only a single ethnicity, a first ethnicity;
a third layer, trained by active learning using a third set of training data comprising third images from only a single ethnicity, a second ethnicity that is different from the first ethnicity; and
a fourth layer, trained by active learning using a fourth set of training data comprising fourth images from only a single ethnicity, a third ethnicity that is different from the first and second ethnicities,
wherein the second, third, and fourth layers are at the same level in the hierarchy of the convolutional neural network, and the second and third layers are above the first layers of the convolutional neural network,
each of the first layers, second layer, third layer, and fourth layer has a single vote, and a diagnosis probability of breast cancer is based on a majority of the votes such that any three of the first layers, second layer, third layer, and fourth layer would constitute a majority.

7. The system of claim 6 wherein
when a majority of the votes is not obtained, the diagnosis probability of breast cancer is based on only the first layers,
a fifth layer and sixth layer are within the first layers of the convolutional neural network, and the sixth layer is above the fifth layer,
the breast image for analysis and an optional identification of an ethnicity of the breast image are input to the fifth layer, the fifth layer extracts first different features in the breast image, the sixth layer stores first weightings for the first different features in the breast image extracted by the fifth layer.

8. The system of claim 7 wherein
when the ethnicity of the breast image for analysis is the first ethnicity, the first weightings for the first different features are input to the second layer and not the third or fourth layers, and given the first weightings from the sixth layer, the second layer outputs second weightings for second different features.

9. The system of claim 8 wherein
a fifth layer and sixth layer are within the first layers of the convolutional neural network, and the sixth layer is above the fifth layer,
the breast image for analysis and is input to the fifth layer, the fifth layer extracts first different features in the breast image, the sixth layer stores first weightings for the first different features in the breast image extracted by the fifth layer.

10. The system of claim 7 wherein
when the ethnicity of the breast image for analysis is the first ethnicity, the first weightings for the first different features are input to the second layer and not the third or fourth layers, and given the first weightings from the sixth layer, the second layer outputs second weightings for second different features.

11. The system of claim 7 wherein
when the ethnicity of the breast image for analysis is the second ethnicity, the first weightings for the first different features are input to the third layer and not the second or fourth layers, and given the first weightings from the sixth layer, the third layer outputs third weightings for third different features.

12. The system of claim 7 wherein
when the ethnicity of the breast image for analysis is the third ethnicity, the first weightings for the first different features are input to the fourth layer and not the second or third layers, and given the first weightings from the sixth layer, the fourth layer outputs fourth weightings for fourth different features.

13. The system of claim 7 wherein
when the ethnicity of the breast image for analysis is not identified, the first weightings for the first different features are input to the second, third, and fourth layers, given the first weightings from the sixth layer, the second layer outputs second weightings for the second different features, given the first weightings from the sixth layer, the third layer outputs third weightings for the third different features, and given the first weightings from the sixth layer, the fourth layer outputs fourth weightings for the fourth different features.

14. A system comprising:
a convolutional neural network comprising a plurality of layers arranged in a hierarchy, wherein an input of the convolutional neural network is at a bottom of the hierarchy of layers and an output is at a top of the hierarchy of layers;
a first plurality of layers of the convolutional neural network which is trained by federated learning using a first set of training data comprising first breast images comprising multiple ethnicities;
a second layer, trained by active learning using a second set of training data comprising second breast images from only a single ethnicity, a first ethnicity; and
a third layer, trained by active learning using a third set of training data comprising third images from only a single ethnicity, a second ethnicity that is different from the first ethnicity,
wherein the second and third layers are at the same level in the hierarchy of the convolutional neural network, and the second and third layers are above the first layers of the convolutional neural network.

15. The system of claim 14 wherein the convolutional neural network comprising the first layers, second layer, and third layer comprises a machine learning model,
a breast image for analysis is input to the input of the convolutional neural network, and the output of the convolutional neural network provides a diagnosis probability of breast cancer.

16. The system of claim 14 wherein a fourth layer and fifth layer are within the first layers of the convolutional neural network, and the fifth layer is above the fourth layer.

17. The system of claim 16 wherein
the breast image for analysis is input to the fourth layer, the fourth layer extracts first different features in the breast image, the fifth layer stores first weightings for the first different features in the breast image extracted by the fourth layer.

18. The system of claim 16 wherein
the first weightings for the first different features are input to the second and third layers,
given the first weightings from the fifth layer, the second layer outputs second weightings for second different features, and
given the first weightings from the fifth layer, the third layer outputs third weightings for third different features.

19. The system of claim 16 wherein the input the convolutional neural network does not include an identification of an ethnicity of the breast image.

20. The system of claim 16 wherein a fourth layer and fifth layer are within the first layers of the convolutional neural network, and the fifth layer is above the fourth layer,
the breast image for analysis and an identification of an ethnicity of the breast image are input to the fourth layer, the fourth layer extracts first different features in the breast image, the fifth layer stores first weightings for the first different features in the breast image extracted by the fourth layer,
when the ethnicity of the breast image for analysis is the first ethnicity, the first weightings for the first different features are input to the second layer, and given the first weightings from the fifth layer, the second layer outputs second weightings for second different features,
when the ethnicity of the breast image for analysis is the second ethnicity, the first weightings for the first different features are input to the third layer, and given the first weightings from the fifth layer, the third layer outputs third weightings for third different features.

* * * * *